(12) United States Patent
Sessions (10) Patent No.: US 7,022,890 B2
(45) Date of Patent: Apr. 4, 2006

(54) WOUND DRESSING SUITABLE FOR INSERTION IN NASAL PASSAGES

(75) Inventor: Robert W. Sessions, Burr Ridge, IL (US)

(73) Assignee: Ferris Pharmaceuticals, Burr Ridge, IL (US)

( * ) Notice: Subject to any disclaimer, the term of this patent is extended or adjusted under 35 U.S.C. 154(b) by 0 days.

(21) Appl. No.: 10/946,687

(22) Filed: Sep. 22, 2004

(65) Prior Publication Data

US 2005/0107731 A1 May 19, 2005

Related U.S. Application Data

(60) Provisional application No. 60/504,843, filed on Sep. 22, 2003.

(51) Int. Cl.
*A61F 13/00* (2006.01)

(52) U.S. Cl. ............................................ 602/46; 604/1
(58) Field of Classification Search ................ 128/857; 604/290, 907, 358, 96, 1; 606/196, 199; 602/46; D24/124
See application file for complete search history.

(56) References Cited

U.S. PATENT DOCUMENTS

| | | | |
|---|---|---|---|
| 3,499,448 A | 3/1970 | Jones | |
| 3,559,646 A | 2/1971 | Mullan | |
| 3,794,024 A | 2/1974 | Kokx et al. | |
| 4,098,728 A | 7/1978 | Rosenblatt | |
| 4,217,900 A | 8/1980 | Wiegner et al. | |
| 4,605,401 A | 8/1986 | Chmelir et al. | |
| 4,646,739 A * | 3/1987 | Doyle ........................ 606/199 |
| 4,884,563 A | 12/1989 | Sessions | |
| 5,011,864 A | 4/1991 | Nielsen et al. | |
| 5,064,653 A | 11/1991 | Sessions et al. | |
| 5,065,752 A | 11/1991 | Sessions et al. | |
| 5,112,348 A | 5/1992 | Glassman | |
| 5,201,326 A | 4/1993 | Kubicki et al. | |
| 5,254,301 A | 10/1993 | Sessions et al. | |
| 5,336,163 A | 8/1994 | DeMane et al. | |
| 5,387,206 A | 2/1995 | Valentine et al. | |
| 5,466,231 A | 11/1995 | Cercone et al. | |
| 5,916,928 A | 6/1999 | Sessions et al. | |
| 5,954,682 A | 9/1999 | Petrus | |
| 6,043,406 A | 3/2000 | Sessions et al. | |
| 6,130,246 A | 10/2000 | Ziegler et al. | |
| 6,183,436 B1 * | 2/2001 | Korteweg et al. ........ 604/96.01 |
| 6,768,040 B1 * | 7/2004 | Sessions et al. ............. 602/56 |

OTHER PUBLICATIONS

Medtronic Xomed Surgical Products, Head and Neck Products brochure of nasal splint and packing systems, applicant first became aware of this material no later than Mar. 26, 2000.

(Continued)

*Primary Examiner*—Kim M. Lewis
(74) *Attorney, Agent, or Firm*—Leydig, Voit & Mayer, Ltd.

(57) ABSTRACT

The invention provides a wound dressing comprising a body and a polymeric film adhered to at least a portion of the body. The body comprises a flexible, porous polyurethane-based foam and a liquid absorbing component. The invention further provides a wound dressing comprising a first body, a second body, and at least one polymeric film disposed between the first and second bodies. The invention additionally provides methods for treating an injury to a patient's nasal passages utilizing a wound dressing according to the invention.

30 Claims, 3 Drawing Sheets

OTHER PUBLICATIONS

Medtronic Xomed Surgical Products, Rhinology Products: Nasal and Sinus Packing catalog pages of nasal packing products, applicant first became aware of this material no later than Mar. 26, 2000.

Medtronic Xomed, excerpt from Medtronic Xomed Product Catalog (2003).

Perry, *Otolaryngology—Head and Neck Surgery*, 127(2): P84-85 (Aug. 2002).

Perry, "Polymeric Membrane Dressings in Nasal Septal Reconstruction," *Annual Meeting of the American Academy of Otolaryngology—Head and Neck Surgery Foundation, Inc.*(Sep. 2002).

Perry, *Otolaryngology—Head and Neck Surgery*, 127(2): P204 (Aug. 2002).

Perry, "Polymeric Membrane Dressings for Endonasal Sinus Surgery, " *Annual Meeting of the American Academy of Otolaryngology—Head and Neck Surgery Foundation, Inc.* (Sep. 2002).

Shippert Medical Technologies, excerpt from Nasal Packing products brochure (2003).

* cited by examiner

WOUND DRESSING SUITABLE FOR INSERTION IN NASAL PASSAGES

CROSS-REFERENCE TO RELATED PATENT APPLICATIONS

This patent application claims the benefit of U.S. Provisional Patent Application No. 60/504,843, filed Sep. 22, 2003.

FIELD OF THE INVENTION

The invention pertains to wound dressings, and more particularly to wound dressings suitable for insertion in the nasal passages.

BACKGROUND OF THE INVENTION

It is sometimes necessary to place dressings in a patient's nasal passages as a means to assist in treating damage to the nasal mucosa. This practice is often called "nasal packing." Nasal packing typically is used to control bleeding of the nasal mucosa following surgical procedures or injury. However, nasal packing also is used to provide support to the nasal structures following surgery (e.g., nasal septal reconstruction (septoplasty) or rhinoplasty) and to prevent reinjury to the nasal mucosa due to nose picking, etc.

A number of different dressings have been used over the years for nasal packing. For example, cotton balls, wedges, and gauze have been applied to the nasal passages to control post-operative bleeding or prevent reinjury of the nasal mucosa. However, cotton-based packing materials can be difficult to remove from the nasal passages without leaving remnants of the dressing (e.g., pieces of the dressing or cotton fibers) in the nasal passages. Furthermore, if the cotton-based packing material is left in the nasal passages for an extended period of time, the packing material can begin to dry out and become adhered to the nasal mucosa. In these cases, if is often difficult to remove the cotton-based packing material without injuring the newly formed nasal mucosa, causing significant pain or discomfort and delaying the healing process.

Another class of dressings widely used in nasal packing is polyvinylacetate (PVA) dressings. While the monolithic nature of PVA dressings can provide for easier handling than cotton-based packing materials, PVA dressings are not without their drawbacks. For example, PVA dressings are relatively brittle, which can make insertion of the dressing into the nasal passages difficult. The relative inflexibility of PVA dressings can also cause considerable discomfort to patients both during and following application of the dressing. Furthermore, upon exposure to an external liquid (e.g., wound exudate), many PVA dressings can swell up to 20 times their original size (e.g., original nominal diameter). While this tendency to swell does provide additional support to the nasal structures, the excessive swelling usually exhibited by PVA dressings can make removal of the dressing more difficult. Lastly, as with cotton-based packing materials, PVA dressings can begin to dry out as the liquid absorbed by the dressing evaporates, thereby causing the dressing to adhere to the nasal mucosa. Removal of the dressing then usually causes injury to the newly formed nasal mucosa accompanied by significant pain or discomfort to the patient.

A need therefore exists for a wound dressing, and related method, that is suitable for insertion in the nasal passages and addresses the foregoing and other problems encountered with the use of existing nasal packing materials. The present invention provides such a wound dressing and method. These and other advantages of the invention, as well as additional inventive features, will be apparent from the description of the invention provided herein.

BRIEF SUMMARY OF THE INVENTION

The invention provides a wound dressing comprising: (i) a body comprising a flexible, porous polyurethane-based foam and a liquid absorbing component, and (ii) a polymeric film adhered to at least a portion of a surface of the body, wherein the body of the dressing is provided in a substantially cylindrical, conical, or frustro-conical shape.

The invention also provides a wound dressing comprising: (i) a body comprising a flexible, porous polyurethane-based foam and a liquid absorbing component, (ii) a polymeric film adhered to at least a portion of a surface of the body, and (iii) a reinforcing film adhered to at least a portion of a surface of the body.

The invention further provides a wound dressing comprising: (i) a first body comprising a flexible, porous polyurethane-based foam and a liquid absorbing component, (ii) a second body comprising a flexible, porous polyurethane-based foam and a liquid absorbing component, and (iii) at least one polymeric film adhered to at least a portion of a surface of the first or second body, wherein the first and second bodies are adhered to each other so that at least a portion of the polymeric film is disposed between the first and second bodies.

The invention also provides a method for treating an injury to a nasal passage, the method comprising the steps of: (a) providing a wound dressing comprising: (i) a body comprising a flexible, porous polyurethane-based foam and a liquid absorbing component, and (ii) a polymeric film adhered to at least a portion of a surface of the body, (b) inserting the wound dressing into a patient's nasal passage so that at least a portion of the wound dressing contacts an injured surface of the nasal passage, (c) retaining the wound dressing in the patient's nasal passage for a time sufficient for the injury to at least partially heal, and (d) removing the wound dressing from the patient's nasal passage.

The invention additionally provides a method for treating an injury to a nasal passage, the method comprising the steps of: (a) providing a wound dressing comprising: (i) a first body comprising a flexible, porous polyurethane-based foam and a liquid absorbing component, (ii) a second body comprising a flexible, porous polyurethane-based foam and a liquid absorbing component, and (iii) at least one polymeric film adhered to at least a portion of a surface of the first or second body, wherein the first and second bodies are adhered to each other so that at least a portion of the polymeric film is disposed between the first and second bodies, (b) inserting the wound dressing into a patient's nasal passage so that at least a portion of the wound dressing contacts an injured surface of the nasal passage, (c) retaining the wound dressing in the patient's nasal passage for a time sufficient for the injury to at least partially heal, and (d) removing the wound dressing from the patient's nasal passage.

DETAILED DESCRIPTION OF THE INVENTION

The invention provides a wound dressing comprising: (i) a body comprising a flexible, porous polyurethane-based foam and a liquid absorbing component, and (ii) a polymeric film adhered to at least a portion of a surface of the body.

The body of the dressing comprises a flexible, porous polyurethane-based foam. As utilized herein, the term "flexible" refers to a foam that may be folded over upon itself without exhibiting cracking and/or breaking. The term "porous" refers to a foam having open pores on at least a portion of its exterior surface. Preferably, the dressing comprises a uniformly porous foam (i.e., a foam having pores of substantially the same size uniformly distributed throughout). The foam preferably exhibits only minimal swelling in the presence of liquids. Typically, upon exposure to a liquid, the foam will swell to less than about 3 times its original nominal thickness or diameter, and preferably less than about 2 times its nominal thickness or diameter. Most preferably, the foam is the polyurethane foam described in U.S. Pat. Nos. 5,064,653, 5,065,752, 5,254,301 and 5,916,928.

The body of the wound dressing also comprises a liquid absorbing component. The liquid absorbing component may be any suitable liquid absorbing component. Suitable liquid absorbing components include, but are not limited to, methylcellulose, guar gum, pectin, karaya gum, chitosan, agar, acacia powder, carrageenan, gelatin, and combinations thereof. Preferably, the liquid absorbing component comprises at least one superabsorbent polymer. Generally, superabsorbent polymers suitable for use in the wound dressing of the invention include polymers that are capable of absorbing about 50 times or more, preferably about 100 times or more, and most preferably about 150 times or more their weight in water. Suitable superabsorbent polymers include, but are not limited to, sodium and aluminum salts of starch grafted copolymers of acrylates and acrylamides and combinations thereof, as well as polyacrylate salts. In particular, superabsorbent polymers suitable for use in the invention include, but are not limited to, poly (D-Glucosamine) from Bentech Laboratories, ARASORB™ 720 from Arakawa Chemical Inc., the WATER LOCK® superabsorbent polymers marketed by Grain Processing Corporation (e.g., WATER LOCK® A-100, A-200, A-222, D-212, D-242, G400, B, C, and H), as well as the poly-2-propionic acid, sodium salt, marketed by Sanyo Corporation under the trademark AQUA KEEP (e.g., AQUA KEEP J-500). The liquid absorbing component preferably is dispersed in the polyurethane foam comprising the body of the wound dressing. More preferably, the liquid absorbing component is uniformly dispersed throughout the polyurethane foam comprising the body of the wound dressing.

The wound dressing of the invention also comprises a polymeric film adhered to at least a portion of a surface of the body of the wound dressing. The polymeric film may comprise any suitable material. Suitable polymeric films include, but are not limited to, medical grade urethane films. Suitable medical grade urethane films can be obtained from Deerfield Urethane, Stevens Urethane, 3M, Avery, Goodyear, Porvair, Inspire, Rexam, Sun Industries, and Lord Corporation. The polymeric film may be any suitable thickness. For example, the thickness of the polymeric film may be about 0.006 mm (0.25 mil) to about 0.076 mm (3 mil). Preferably, the thickness of the polymeric film is about 0.015 mm to about 0.03 mm (e.g., about 0.026 mm (1.0 mil)), more preferably about 0.02 mm (0.75 mil).

In certain embodiments, the polymeric film may be a semipermeable, polymeric film. As utilized herein, the term "semipermeable" refers to a film that allows the exchange of gases (e.g., $O_2$, $CO_2$, and water vapor) across the film, while providing a barrier against environmental contaminants (e.g., bacteria). In such embodiments, the semipermeable, polymeric film preferably is selected to maximize the moisture vapor transmission rate (MVTR) between the wound dressing and the surrounding environment. For example, the MVTR preferably may be about 90 to about 3,000 grams per square meter per 24 hours (e.g., about 200 to about 2500 grams per square meter per 24 hours, about 400 to about 2000 grams per square meter per 24 hours, about 500 to about 1500 grams per square meter per 24 hours, about 600 to about 1200 grams per square meter per 24 hours, or about 700 to about 900 grams per square meter per 24 hours).

The polymeric film may be adhered to at least a portion of any suitable surface of the body of the wound dressing. In certain embodiments, at least a portion of the polymeric film is coextensive with at least one surface of the body. The polymeric film may be adhered to a surface of the body of the wound dressing in any suitable manner. Generally, the polymeric film may be adhered to a surface of the body using a suitable (e.g., medical grade) adhesive. Alternatively, and preferably, the polymeric film may be adhered to a surface of the body by casting the body of the wound dressing on the polymeric film during the production of the wound dressing.

The body of the dressing may be provided in any suitable shape. For example, the body of the dressing may be provided in a substantially rectangular or square shape (i.e., one of the major faces of the dressing is substantially rectangular or square in shape). In a preferred embodiment, the body of the dressing is provided in a substantially cylindrical, conical, or frustro-conical shape. Generally, the dressing is provided in a shape suitable for insertion in the nasal passage of a patient.

Figure 1:
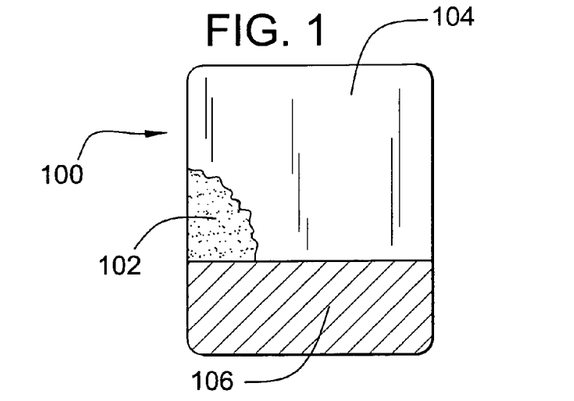
FIG. 1 is a plan view of a wound dressing according to an aspect of the invention, wherein the body of the wound dressing is provided in a substantially rectangular shape.

FIG. 1 depicts one embodiment of the wound dressing of the invention. The wound dressing 100 comprises a body 102, which body 102 comprises a flexible, uniformly porous polyurethane-based foam and a liquid absorbing component. A polymeric film 104, which is shown cut-away to expose the body 102, is adhered to a surface of the body 102 of the wound dressing 100. A reinforcing film 106 is also adhered to a surface of the body 102.

Figure 2:
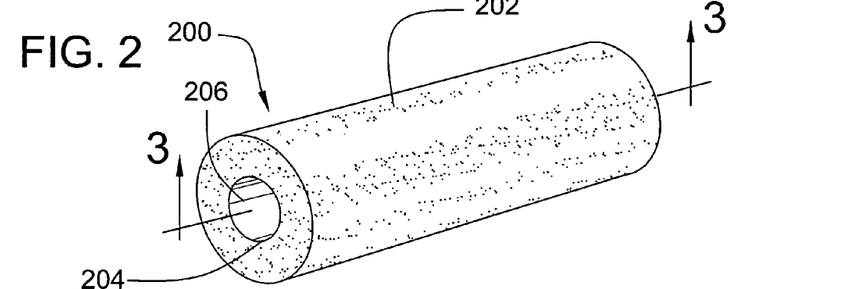
FIG. 2 is a perspective view of a wound dressing according to an aspect of the invention, wherein the wound dressing is provided in a substantially cylindrical shape.
Figure 3:
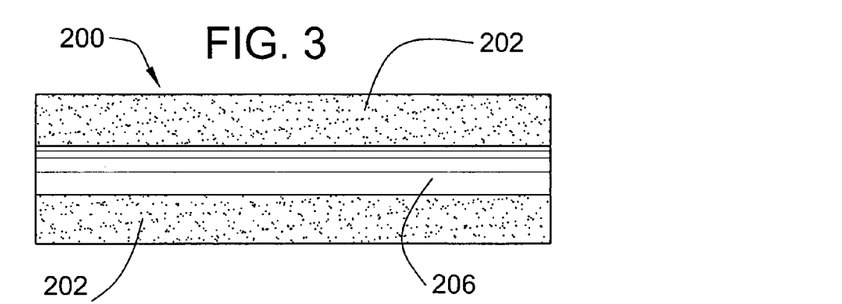
FIG. 3 is a sectional view of the wound dressing shown in FIG. 2 along broken line III.
Figure 4:
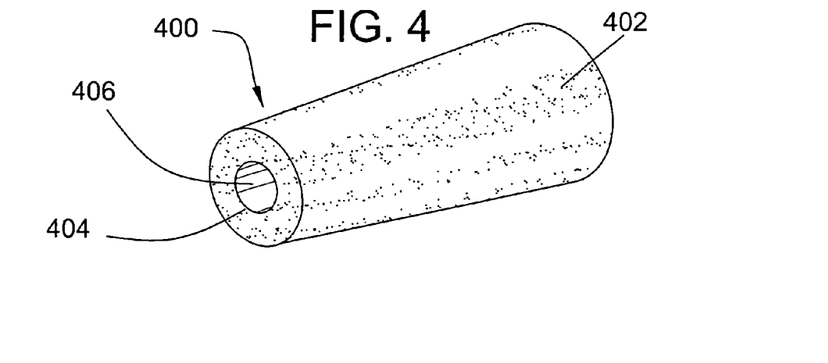
FIG. 4 is a perspective view of a wound dressing according to an aspect of the invention, wherein the wound dressing is provided in a substantially frustro-conical shape.

When the dressing is provided in a substantially cylindrical, conical, or frustro-conical shape, the body of the wound dressing preferably comprises a passage therethrough and the polymeric film is adhered to the inside surface of the body formed by the passage. Preferably, the passage is provided through the longitudinal axis of the body of the wound dressing. FIG. 2 depicts such an embodiment of the wound dressing of the invention. The wound dressing 200 comprises a body 202, which body 202 comprises a flexible, uniformly porous polyurethane-based foam and a liquid absorbing component. The body 202 of the dressing is provided in a substantially cylindrical shape having a passage 206 running along the length of the body 202. A polymeric film 204 is adhered to the inside surface of the body 202 formed by the passage 206. FIG. 3 is a sectional view of the wound dressing depicted in FIG. 2 showing the relationship of the body 202, the polymeric film 204, and the passage 206. FIG. 4 depicts a similar embodiment of the wound dressing of the invention, except that the body of the wound dressing is provided in a substantially frustro-conical shape. In particular, the wound dressing 400 comprises a body 402, which body 402 comprises a flexible, uniformly porous polyurethane-based foam and a liquid absorbing component. The body 402 of the dressing is provided in a substantially frustro-conical shape having a passage 406 running along the length of the body 402. A polymeric film 404 is adhered to the inside surface of the body 402 formed by the passage 406.

The wound dressing may be provided in any suitable size. Generally, the wound dressing is dimensioned so that it may be easily inserted into and removed from the nasal passage of a patient. To that end, it will be understood that the appropriate size of the wound dressing will depend upon several factors, such as, for example, the size of the patient's nasal passages and the portion of the nasal passage into which the wound dressing is inserted (e.g., the ethmoidal and middle meatal region between the middle and inferior turbinates, adjacent to the inferior turbinate, or adjacent to the nasal septum). In particular, the body of the wound dressing may be provided in any suitable thickness. In certain embodiments, the body of the dressing may be provided in a thickness of about 0.1 to about 1.0 cm, preferably about 0.1 to about 0.6 cm, more preferably about 0.1 to about 0.5 cm, still more preferably about 0.2 to about 0.4 cm, and most preferably about 0.3 cm (e.g., about 0.25 to about 0.35 cm). The wound dressing of the invention may be provided in any suitable length or width. Typically, the body of the wound dressing is provided in a length of about 1 to about 10 cm (e.g., about 2 to about 10 cm), preferably about 3 to about 9 cm, and more preferably about 4 to about 8 cm (e.g., about 4.5 to about 7.75 cm). The body of the wound dressing typically is provided in a width (at its widest point) of about 1 to about 8 cm, preferably about 2 to about 7 cm, more preferably about 2.5 to about 6 cm, and most preferably about 3 to about 5.5 cm. It will also be understood that the aforementioned dimension ranges (i.e., thickness, length, and width of the body of the wound dressing) may be combined to provide a wound dressing of suitable size.

The body of the wound dressing may further comprise an adjuvant. Preferably, the adjuvant is dispersed (e.g., uniformly dispersed) in the foam comprising the body of the wound dressing. Preferably, the adjuvant is water-soluble so that it may be readily released from the wound dressing upon contact with an external liquid (e.g., wound exudate). It is also desirable that the adjuvant be capable of contacting the nasal mucosa without adverse side effects. Furthermore, the adjuvant preferably comprises a chemical compound that will have the ability to open the pores of the nasal mucosa to achieve a demulcent effect to relieve pain and/or irritation and to achieve an emollient effect to soften the tissue and prevent maceration. It is also preferred that the adjuvant be compatible with therapeutic or other agents which may be carried by the adjuvant for subsequent delivery to the situs of application. Adjuvants suitable for use in the wound dressing of the invention include, but are not limited to, mono, di and polyhydric alcohols. Generally, the molecular weight of the alcohols should be less than about 1000. Examples of mono alcohols suitable for use as an adjuvant include, but are not limited to, ethyl alcohol and isopropyl alcohol. Suitable diols include propylene glycol, polyethylene glycol, and polypropylene glycol. Polyhydric alcohols suitable for use as an adjuvant in the invention include, but are not limited to, glycerin, 1,2,4-butanetriol, trimethylolpropane, pentaerythritol and sorbitol. The adjuvant may also comprise a mixture of two or more of the aforementioned alcohols. Preferably, the adjuvant comprises glycerin.

The body of the wound dressing preferably comprises a wetting agent. Typically, the wetting agent is dispersed in the foam comprising the body of the wound dressing. Suitable wetting agents include, but are not limited to, surfactants, ethoxylated sorbitan fatty acid esters, glycerol esters, polyglycerol esters, and silicone fluids. Preferably, the wetting agent is a surfactant (e.g., non-ionic surfactant). Surfactants suitable for use as a wetting agent in the wound dressing of the invention include, but are not limited to, the block copolymers of ethylene oxide and propylene oxide sold by BASF Corporation under the trademark PLURONIC (e.g., PLURONIC F-68 and PLURONIC L-62). Preferably, the surfactant is capable of exhibiting a wound cleansing action without causing tissue damage. Furthermore, a portion of the surfactant preferably is released from the wound dressing upon exposure to an external fluid (e.g., wound exudate), thereby cleansing the tissue while the wound dressing is in place.

The wetting agent may be present in the body of the dressing in any suitable amount. Generally, the wetting agent is present in the body of the dressing in an amount sufficient to provide substantially uniform wettability of the foam. Preferably, the wetting agent is present in the body of the dressing in an amount of about 1 to about 10% by weight, preferably from about 5% to about 7% by weight, based on the weight of the foam comprising the body of the dressing.

Figure 5:
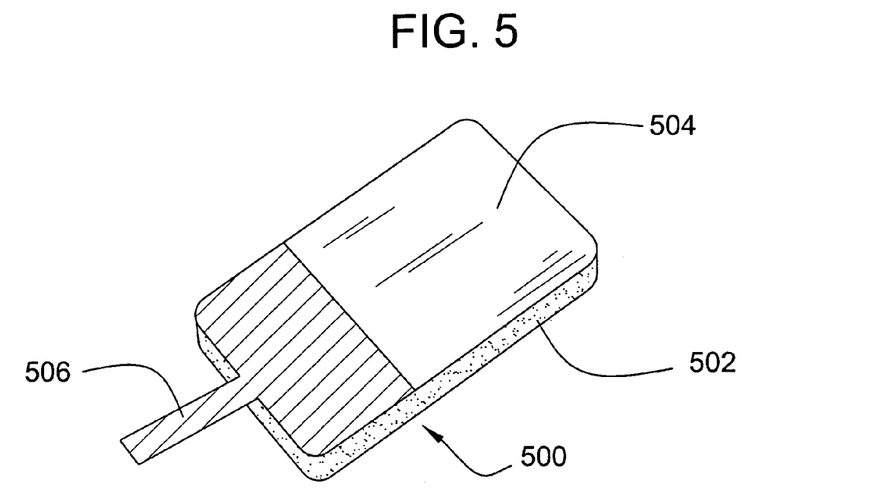
FIG. 5 is a perspective view of a wound dressing according to an aspect of the invention, wherein a reinforcing film extends beyond a surface of the body to form a "tab" to aid in the stabilization of and/or removal of the dressing.

The wound dressing of the invention may further comprise a reinforcing film adhered to at least a portion of a surface of the body. Such a reinforcing film may be used to protect against tearing of the wound dressing upon removal from the nasal passages. The reinforcing film may comprise any suitable material (e.g., medical grade urethane film). The reinforcing film may be provided in any suitable size and/or shape. However, the thickness of the reinforcing film should be selected to provide sufficient mechanical strength to withstand the forces necessary to remove the wound dressing from the nasal passages. For example, the thickness of the reinforcing film can be about 0.025 mm (1 mil) to about 0.1 mm (4 mil), preferably about 0.038 mm (1.5 mil) to about 0.08 mm (3 mil), and more preferably about 0.05 mm (2 mil). Furthermore, the characteristics of the reinforcing film (e.g., thickness or composition) may be selected to impart desired spring characteristics to the wound dressing so that the dressing applies the desired amount of force to the nasal mucosa when it is folded and inserted into a nasal passage. Preferably, the reinforcing film is adhered to at least a portion of the same surface to which the polymeric film is adhered. The reinforcing film may also be substantially coextensive with at least one surface of the body of the dressing (e.g., the same surface to which the polymeric film is adhered). The reinforcing film preferably extends beyond a surface of the body of the wound dressing. Such a "tab" of the reinforcing film may be used to aid in the stabilization of the wound dressing within the nasal passages (e.g., the tab can be adhered to the patient's skin to prevent migration of the wound dressing within the patient's nasal passage) and/or the removal of the wound dressing from the nasal passages of a patient. FIG. 5 depicts such an embodiment of the wound dressing of the invention. The wound dressing 500 comprises a body 502, which body 502 comprises a flexible, uniformly porous polyurethane-based foam and a liquid absorbing component. A polymeric film 504 is adhered to a surface of the body 502, and a reinforcing film 506 is adhered to a surface of the body 502. The reinforcing film 506 also extends beyond a surface of the body 502 of the wound dressing 500, thereby providing a "tab" to assist in stabilization and/or removal of the wound dressing 500 from a nasal passage.

Alternatively, the reinforcing film may be replaced with an element having a greater degree of rigidity. For example, a metal or plastic element (e.g., sheet) may be adhered to a surface of the wound dressing in place of the reinforcing film. The characteristics of the element (e.g., thickness or composition) may be selected to impart desired spring characteristics to the wound dressing so that the dressing applies the desired amount of force to the nasal mucosa when it is folded and inserted into a nasal passage.

Figure 6:
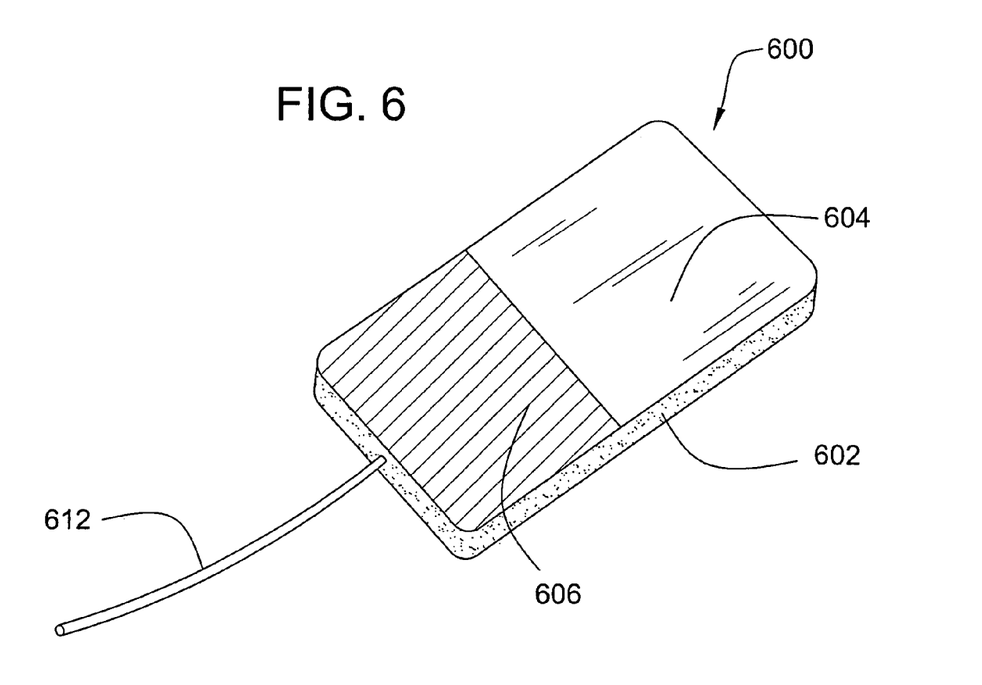
FIG. 6 is a perspective view of a wound dressing according to an aspect of the invention, wherein the wound dressing comprises a tether extending from the dressing to assist in the stabilization or and/or removal of the dressing.

The wound dressing of the invention may further comprise a tether attached to the dressing and extending from one end of the dressing to assist in stabilization and/or removal of the dressing from a body cavity. FIG. 6 depicts such an embodiment of the wound dressing of the invention. The wound dressing 600 comprises a body 602, which body 602 comprises a flexible, uniformly porous polyurethane-based foam and a liquid absorbing component. A polymeric film 604 is adhered to a surface of the body 602, and a reinforcing film 606 is adhered to a surface of the body 602. A tether 612 is attached to the body 602 of the wound dressing 600. The tether may comprise any medically suitable material (e.g., cotton, nylon, etc.) of sufficient strength to avoid breakage upon removal of the wound dressing, and may be attached to the body of the wound dressing by any suitable means. Typically, the tether is cast within the body of the wound dressing during the manufacturing process, thereby securely anchoring the tether to the wound dressing.

The wound dressing of the invention may further comprise various additional medicaments, cosmetics, and therapeutic agents. Preferably, any additional medicament, cosmetic, or therapeutic agent is released from the dressing upon exposure to an external fluid (e.g., wound exudate). Typically, any such additional medicament, cosmetic, or therapeutic agent will be "carried" from the wound dressing by the adjuvant. This release allows the transmission of such medicament, cosmetic, or therapeutic agent to the tissue adjacent the wound dressing of the invention, further assisting in the beneficial treatment of the wound. Therapeutic agents suitable for incorporation into the wound dressing include Collasol 2400, Crotein SPA, Cromoist HYA, Crotein CAA and hydrocortisone acetate. Suitable cosmetic agents include, but are not limited to, European Collagen Complex, Capture Complex Liposomes, Sardo® bath oil, a hand lotion sold under the trademark Jergens®, Noxzema® skin cream, Oil of Olay® BF, Keri® lotion, Vaseline® herbal and aloe lotion, Ben Gay® ointment, and Retin-A® cream.

The invention further provides a wound dressing comprising: (i) a first body comprising a flexible, uniformly porous polyurethane-based foam and a liquid absorbing component, (ii) a second body comprising a flexible, uniformly porous polyurethane-based foam and a liquid absorbing component, and (iii) at least one polymeric film adhered to at least a portion of a surface of the first or second body, wherein the first and second bodies are adhered to each other so that at least a portion of the polymeric film is disposed between the first and second bodies. The other characteristics of this embodiment of the wound dressing of the invention (e.g., the foam, the liquid absorbing component, the polymeric film, the size and/or shape of the bodies) can be the same as set forth above for the first embodiment of the wound dressing of the invention.

As noted above, the first and second bodies are adhered to each other so that the at least a portion of the at least one polymeric film is disposed between the first and second bodies. The first and second bodies may be adhered to each other in any suitable manner. Generally, the first and second bodies are adhered to each other using a suitable (e.g., medical grade) adhesive. Alternatively, the first and/or second body may be cast directly onto the other body in such a way that at least a portion of the at least one polymeric film is disposed between the two resulting bodies. Preferably, the polymeric film is entirely disposed between the first and second bodies.

Figure 7:
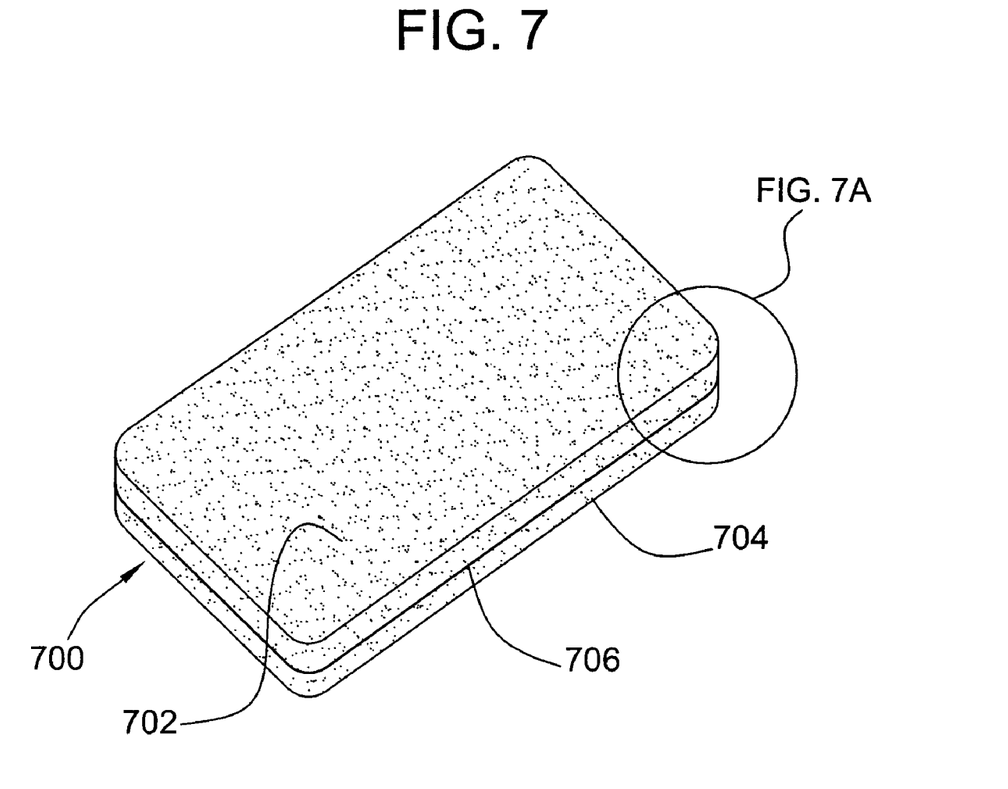
FIG. 7 is a perspective view of a wound dressing according to an aspect of the invention, wherein the wound dressing comprises first and second bodies adhered to each other with a polymeric film disposed between the first and second bodies.
Figure 7A:
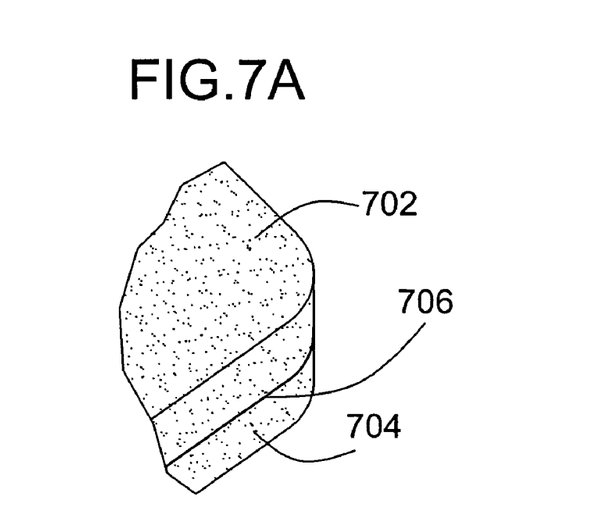
FIG. 7A is a detail view of the wound dressing shown in FIG. 7.

FIG. 7 depicts an embodiment of the wound dressing of the invention. In particular, the wound dressing 700 comprises a first body 702 and a second body 704, which bodies comprise a flexible, uniformly porous polyurethane-based foam and a liquid absorbing component. The wound dressing 700 further comprises a polymer film 706 adhered to the first body 702 and the second body 704 and disposed between said first body 702 and said second body 704.

The invention additionally provides methods for treating an injury to a patient's nasal passage utilizing a wound dressing according to the invention. The methods generally comprise the steps of: (a) providing a wound dressing according to the invention, (b) inserting the wound dressing into a patient's nasal passage so that at least a portion of the wound dressing contacts an injured surface of the nasal passage, (c) retaining the wound dressing in the patient's nasal passage for a time sufficient for the injury to at least partially heal, and (d) removing the wound dressing from the patient's nasal passage.

In one embodiment, the invention provides a method for treating an injury to a nasal passage, the method comprising the steps of: (a) providing a wound dressing comprising: (i) a body comprising a flexible, porous polyurethane-based foam and a liquid absorbing component, and (ii) a polymeric film adhered to at least a portion of a surface of the body, (b) inserting the wound dressing into a patient's nasal passage so that at least a portion of the wound dressing contacts an injured surface of the nasal passage, (c) retaining the wound dressing in the patient's nasal passage for a time sufficient for the injury to at least partially heal, and (d) removing the wound dressing from the patient's nasal passage. The other characteristics of the wound dressing utilized in this method embodiment of the invention (e.g., the foam, the liquid absorbing component, the polymeric film, the size and/or shape of the bodies) can be the same as set forth above for the wound dressing of the invention.

In another embodiment, the invention provides a method for treating an injury to a nasal passage, the method comprising the steps of: (a) providing a wound dressing comprising: (i) a first body comprising a flexible, porous polyurethane-based foam and a liquid absorbing component, (ii) a second body comprising a flexible, porous polyurethane-based foam and a liquid absorbing component, and (iii) at least one polymeric film adhered to at least a portion of a surface of the first or second body, wherein the first and second bodies are adhered to each other so that at least a portion of the polymeric film is disposed between the first and second bodies, (b) inserting the wound dressing into a patient's nasal passage so that at least a portion of the wound dressing contacts an injured surface of the nasal passage, (c) retaining the wound dressing in the patient's nasal passage for a time sufficient for the injury to at least partially heal, and (d) removing the wound dressing from the patient's nasal passage. The other characteristics of the wound dressing utilized in this method embodiment of the invention (e.g., the foam, the liquid absorbing component, the polymeric film, the size and/or shape of the bodies) can be the same as set forth above for the wound dressing of the invention.

The wound dressing may be inserted into the nasal passage using any suitable method. Generally, when the wound dressing of the invention is provided in a substantially flat shape (e.g., when the dressing is provided in rectangular or square shape), the wound dressing may be folded before insertion into the nasal passage. Typically, when folded, the wound dressing is folded along its longest dimension (i.e., length) so that the polymeric film is disposed between the two folded halves of the wound dressing. Alternatively, a dressing that is provided in a substantially flat shape (e.g., a substantially rectangular or square shape) may be rolled or twisted before insertion to the nasal passage. Typically, the wound dressing is rolled or twisted so that the smallest amount of the polymeric film contacts the nasal mucosa when the wound dressing is inserted into the nasal passage. When the wound dressing comprises a first body and a second body having a polymeric film disposed between the first and second bodies, the wound dressing may be folded, when necessary, along any suitable dimension (e.g., length or width). In certain circumstances, the wound dressing may be lubricated prior to insertion into the nasal passages. In such embodiments, the wound dressing may be lubricated using any suitable medical lubricant (e.g., a cortisporin ointment). The wound dressing of the invention preferably is inserted into the appropriate portion of the nasal passage so that the foam body of the wound dressing contacts an injured surface of the nasal passage (e.g., injured nasal mucosa). Following certain procedures, it is sometimes necessary to place a nasal splint (e.g., silastic nasal splint) or a breathing tube in the nasal passage. In these circumstances, the wound dressing of the invention may be inserted above and/or below the nasal splint or around the breathing tube.

Typically, the wound dressing of the invention is allowed to remain in the nasal passages for a period of time sufficient to allow the nasal mucosa to partially heal (e.g., about 5 days following insertion). The wound dressing of the invention may be removed by any suitable means. For example, when the wound dressing comprises a tether extending from one end of the wound dressing, the wound dressing may be removed by gently pulling on the tether. Alternatively, when the wound dressing comprises a reinforcing film that extends beyond the body of the wound dressing, the wound dressing may be removed by gently pulling on the "tab" formed by the portion of the reinforcing film that extends beyond the body of the wound dressing. Preferably, the wound dressing of the invention is removed from the nasal passage by gently pulling on a portion of the wound dressing (e.g., the body, the reinforcing film, or the tether) using a forceps.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A wound dressing having an exterior portion adapted to contact a wound comprising:
   (i) a first body comprising a flexible, porous polyurethane-based foam and a liquid absorbing component,
   (ii) a second body comprising a flexible, porous polyurethane-based foam and a liquid absorbing component, and
   (iii) at least one polymeric film intermediate of at least a portion of a surface of the first body and at least a portion of a surface of the second body.
   wherein the first and second bodies are adhered to each other so that at least a portion of the polymeric film is disposed between the first and second bodies, and
   wherein at least a portion of the exterior of the first and second bodies comprise the exterior portion of the wound dressing and are capable of absorbing liquid.

2. The wound dressing of claim 1, wherein the liquid absorbing components comprise a superabsorbent polymer.

3. The wound dressing of claim 2, wherein the first and second bodies further comprise an adjuvant dispersed in the foam.

4. The wound dressing of claim 3, wherein the adjuvant comprises glycerin.

5. The wound dressing of claim 4, wherein the first and second bodies further comprise a surfactant dispersed in the foam.

6. The wound dressing of claim 1, wherein the first and second bodies further comprise an adjuvant dispersed in the foam.

7. The wound dressing of claim 6, wherein the adjuvant comprises glycerin.

8. The wound dressing of claim 1, wherein the first and second bodies further comprise a surfactant dispersed in the foam.

9. The wound dressing of claim 1, wherein the dressing further comprises a tether attached to the dressing and extending from one end of the dressing to assist in stabilization of the dressing within a body cavity or removal of the dressing from a body cavity.

10. A method for treating an injury to a nasal passage, the method comprising the steps of:
    (a) providing a wound dressing having an exterior portion adapted to contact a wound comprising:
        (i) a first body comprising a flexible, porous polyurethane-based foam and a liquid absorbing component,
        (ii) a second body comprising a flexible, porous polyurethane-based foam and a liquid absorbing component, and
        (iii) a polymeric film intermediate of at least a portion of a surface of the first body and at least a portion of a surface of the second body, wherein at least a portion of the exterior of the first and second bodies comprise the exterior portion of the wound dressing and are capable of absorbing liquid,
    (b) inserting the wound dressing into a patient's nasal passage so that at least a portion of the exterior portion of the wound dressing contacts an injured surface of the nasal passage.
    (c) retaining the wound dressing in the patient's nasal passage for a time sufficient for the injury to at least partially heal, and
    (d) removing the wound dressing from the patient's nasal passage.

11. The method of claim 10, wherein the liquid absorbing component comprises a superabsorbent polymer.

12. The method of claim 10, wherein the wound dressing further comprises a reinforcing film adhered to at least a portion of a surface of the body.

13. The method of claim 10, wherein the body of the dressing is provided in a substantially cylindrical, conical, or frustro-conical shape.

14. The method of claim 10, wherein the wound dressing is folded along its longest dimension prior to insertion into the patient's nasal passage.

15. The method of claim 14, wherein the wound dressing is folded so that the polymeric film is disposed between the two folded halves of the wound dressing.

16. The method of claim 10, wherein the wound dressing is rolled or twisted prior to insertion into a patient's nasal passage.

17. A method for treating an injury to a nasal passage, the method comprising the steps of:
    (a) providing a wound dressing comprising:
        (i) a first body comprising a flexible, porous polyurethane-based foam and a liquid absorbing component,
        (ii) a second body comprising a flexible, porous polyurethane-based foam and a liquid absorbing component, and
        (iii) at least one polymeric film adhered to at least a portion of a surface of the first or second body, wherein the first and second bodies are adhered to each other so that at least a portion of the polymeric film is disposed between the first and second bodies,
    (b) inserting the wound dressing into a patient's nasal passage so that at least a portion of the wound dressing contacts an injured surface of the nasal passage,
    (c) retaining the wound dressing in the patient's nasal passage for a time sufficient for the injury to at least partially heal, and
    (d) removing the wound dressing from the patient's nasal passage.

18. The method of claim 17, wherein the liquid absorbing components comprise a superabsorbent polymer.

19. The method of claim 17, wherein the first and second bodies are provided in a substantially cylindrical, conical, or frustro-conical shape.

20. The method of claim 17, wherein the wound dressing is folded prior to insertion into the patient's nasal passage.

21. The method of claim 17, wherein the wound dressing comprises an external portion, and wherein at least a portion of the exterior portion of the wound dressing contacts the injured surface of the nasal passage during step (c).

22. The method of claim 21, wherein the liquid absorbing components comprise a superabsorbent polymer.

23. The method of claim 22, wherein the first and second bodies further comprise an adjuvant dispersed in the foam.

24. The method of claim 23, wherein the adjuvant comprises glycerin.

25. The method of claim 23, wherein the first and second bodies further comprise a surfactant dispersed in the foam.

26. The method of claim 17, wherein the dressing further comprises a tether attached to the dressing and extending from one end of the dressing to assist in stabilization of the dressing within a body cavity or removal.

27. The method of claim 17, wherein the wound dressing is folded along its longest dimension prior to insertion into the nasal passage.

28. The method of claim 17, wherein the wound dressing is folded so that the polymeric film is disposed between the two folded halves of the wound dressing.

29. The method of claim 17, wherein the wound dressing is rolled or twisted prior to insertion into the nasal passage.

30. The method of claim 17, wherein the polymeric film is semipermeable.

* * * * *